(12) United States Patent
Liu et al.

(10) Patent No.: US 8,343,741 B2
(45) Date of Patent: Jan. 1, 2013

(54) PELLETIZATION PROCESS TO CONTROL FILAMENTOUS FUNGI MORPHOLOGY FOR ENHANCED REACTOR RHEOLOGY BIOPRODUCT FORMATION

(75) Inventors: Yan Liu, East Lansing, MI (US); Wei Liao, East Lansing, MI (US); Craig Frear, Pullman, WA (US); Shulin Chen, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 849 days.

(21) Appl. No.: 12/338,122

(22) Filed: Dec. 18, 2008

(65) Prior Publication Data

US 2010/0159557 A1     Jun. 24, 2010

(51) Int. Cl.
*C12N 11/00* (2006.01)
*C12N 3/00* (2006.01)

(52) U.S. Cl. ........................................ 435/174; 435/242

(58) Field of Classification Search .................. 435/174, 435/242

See application file for complete search history.

(56) References Cited

U.S. PATENT DOCUMENTS

| | | | |
|---|---|---|---|
| 2,761,246 | A | 9/1956 | Szuecs |
| 4,668,512 | A | 5/1987 | Lewis et al. |
| 4,767,441 | A | 8/1988 | Walker et al. |
| 4,803,800 | A | 2/1989 | Romaine et al. |
| 4,818,530 | A | 4/1989 | Marois et al. |
| 5,068,105 | A | 11/1991 | Lewis et al. |
| 5,185,255 | A | 2/1993 | Endo et al. |
| 6,143,549 | A | 11/2000 | Lamar et al. |
| 6,255,085 | B1 | 7/2001 | Chen et al. |

*Primary Examiner* — Chih-Min Kam
(74) *Attorney, Agent, or Firm* — Whitham Curtis Christofferson & Cook, PC

(57) ABSTRACT

Filamentous fungi are grown in pellet form by culturing the filamentous fungi in liquid culture under one or more of the following conditions: 1) with addition of particulate substrates: 2) using spores which have been stored for a period of time prior to inoculation; and 3) using high spore inoculum concentrations.

19 Claims, 10 Drawing Sheets

PELLETIZATION PROCESS TO CONTROL FILAMENTOUS FUNGI MORPHOLOGY FOR ENHANCED REACTOR RHEOLOGY BIOPRODUCT FORMATION

BACKGROUND OF THE INVENTION

1. Field of the Invention

The invention generally relates to methods of growing filamentous fungi in pellet form in liquid culture. Improved methods for growing filamentous fungi in pellet form in liquid culture include one or more of: 1) addition of a particulate substrate; 2) using spores which have been stored for a period of time prior to inoculation; and 3) using high spore inoculum concentrations, thereby increasing fungal mass and bioproduct formation.

2. Background of the Invention

Filamentous fungal fermentation is widely used to commercially produce useful products such as organic acids, enzymes, antibiotics, and cholesterol lowering drugs (statins) (Cao et al., 1996; Casas Lopez et al., 2004, Chahal, 1985; Hang, 1989; Papagianni, 2004; Schuurmans et al., 1956; Steel et al., 1954). Fungi can be grown in submerged cultures in several different morphological forms: suspended mycelia, clumps, or pellets (Metz et al., 1977). Many studies have discussed the advantages and disadvantages of growth morphologies in terms of different products (Calam, 1976; Konig et al., 1982; Martin et al., 1952).

Without pelletization, filamentous fungi form cotton-like mycelia in liquid culture. This is problematic, because mass transfer of nutrients and products in cotton-like mycelia may be slow due to the large size of mycelial clumps. In bioreactors, clump mycelia increases the viscosity of the medium and wraps around inside elements of the reactor, such as baffles, impellers, heat exchanger, electrode, etc. All of these factors eventually lead to low yield and low productivity. Compared with clump-like mycelia, fungal pellets have a much larger specific surface area which reduces the mass transfer limitations. The pellet morphology also has a beneficial effect on broth rheology, which in return affects momentum, mass and heat transfer in the reactor. Consequently, efficiency of mixing and aeration and cooling systems are enhanced (Charles et al., 1978; Olsvik et al., 1994). It has been reported that higher yields and productivity of lactic acid were obtained using pelletized morphology (Liu et al., 2006a, Yin et al., 1998). Another advantage of fungal pellet fermentation is that the pellets make it possible to perform high biomass concentration cultures to enhance the productivity (Yin et al., 1998; Liu et al., 2006a).

Factors such as medium compositions, pH, medium shear, culture temperature, agitation, additives, oxygen tension, surface-active agents, and medium viscosity have been implicated in pellet formation (Metz et al., 1977; Nielsen et al., 1996; Papagianni, 2004; Znidarsic et al., 1998). Several processes have been able to control the media composition to induce fungal pellet formation. However, pelleting processes described to date have some major disadvantages for industrial applications, e.g. complicated medium compositions which are only suitable for a small range of inoculum, strict reaction conditions, and applicability only to individual strains. For individual strains, each factor has a different importance to the growth morphologies. Some strains such as *Rhizopus* sp. need strong agitation to form pellets, while some strains such as *Penicillium chrysogenum* require high pH to form pellets (Metz et al., 1977). Due to the numerous factors affecting pellet formation and growth, presently known methods for culturing fungi in pellet form are thus complex, unpredictable and difficult to adapt to industrial applications.

It has been reported that polymer additives such as anionic polymers of carbopol-934 (carboxypolymethylene) and Reten (polyacrylate) can decrease the agglutination of spores and produce a much more dispersed growth which can increase the pellet number with an accompanying decrease of pellet size and density (Metz, 1977). However, such polymer additives cannot be digested by fungi and become "contaminants" that must be removed prior to or during bioproduct isolation. In addition, some polymer additives are very expensive, while others may be strictly regulated, for example, when used for the production of drugs.

U.S. Pat. No. 6,490,824 (Maekawa et al., 2002) describes the use of water-insoluble growth supporting material to serve as the core of fungus aggregates when culturing basidiomycetous fungus in a liquid culture medium. However, this methodology narrowly targets basidiomycetes, and the patent states that the growth-promoting and stabilizing effect is said to be specific to crushed sugarcane, sugarcane bagasse, wheat bran and pine tree tissues, severely limiting its application.

U.S. Pat. No. 2,850,841 (Szuecs, 1958) describes the liquid culture of edible mushroom mycelia using a support material such as cereal flour (e.g. Cream of Wheat), starch, etc. However, the results of the method were highly variable and inconsistent, ranging from "caviar or pearl-like pellets" to "larger lump- or ball-like masses". In effect, the method provides little or no control over fungus morphology. Such methodology was geared to the production of edible fungi, would not necessarily apply to other fungi, and would not be suitable for the production of fungus bioproducts in commercial reactors.

The prior art has thus-far failed to provide methods to predictably and consistently grow filamentous fungi in pellet form in liquid culture in a manner that is readily implemented in commercial reactors.

SUMMARY OF THE INVENTION

Embodiments of the invention provide an improved method for not only producing but controlling the pellet morphology of filamentous fungi so that enhancements in bioproduct production can be attained. The method relates to utilization of several key control parameters that have not been previously studied or known to exist within the art. These control parameters include but are not limited to: (1) use of a particulate substrate as a nucleonic source; (2) control of the spore storage time prior to pellet production; and (3) control of concentration of spores in the inoculum. Manipulation one or more of these three control parameters in a novel manner, along with but not requiring control of additional known parameters (such as pH, agitation speed, etc.) allows for the consistent production of pellet morphology of a particular desired shape, size, density (porosity), stage of maturation (e.g. bud vs mature), etc. The technology is applicable across multiple strains of filamentous fungi for production of multiple bioproducts.

Beyond assisting in fermentor rheological concerns and improving mass transfer for ultimate increases in bioproduct yield, productivity and operation costs, this consistent, inexpensive, and easily applicable pellet process is commercially advantageous in the following additional manners. First, the nucleonic source is biodegradable, thus leaving no remaining residue to complicate downstream separation. Second, the nucleonic source also serves as an initial nutritive source, thus reducing the cost of nutritive additions. Third, the desirably shaped pellets can be readily settled for ease of later downstream separation and reuse. Lastly, the pellet production process is easily scaled as the pellet process may be done in a dedicated pellet reactor so that consistent and controlled pellet properties can be attained which can then be used as a source to feed numerous commercial-scale production fermentors.

The invention also provides a mathematical model for analyzing and/or predicting the outcome of manipulation of various parameters on pellet size, shape, porosity, maturation, etc. The method involves the use of a linear regression model, as described herein.

DETAILED DESCRIPTION OF THE PREFERRED EMBODIMENTS OF THE INVENTION

Figures 1A, 1B:
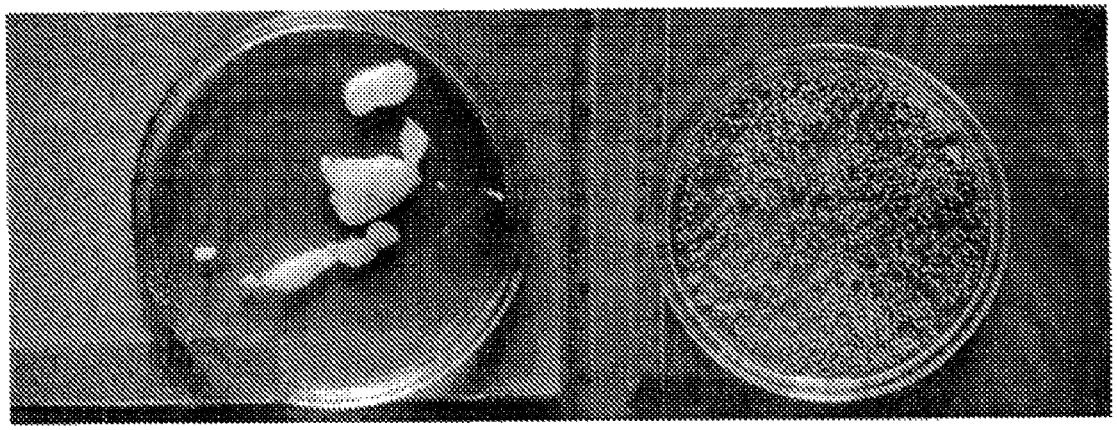
FIGS. 1A and B. Morphology of fungal biomass A, without added biodegradable polymer (12 g/L of PDB and an inoculum spore concentration of $1\times10^8$ spore/L); and B, without biodegradable polymer (12 g/L of PDB and inoculum spore concentration of $1\times10^9$ spore/L).
Figure 2:
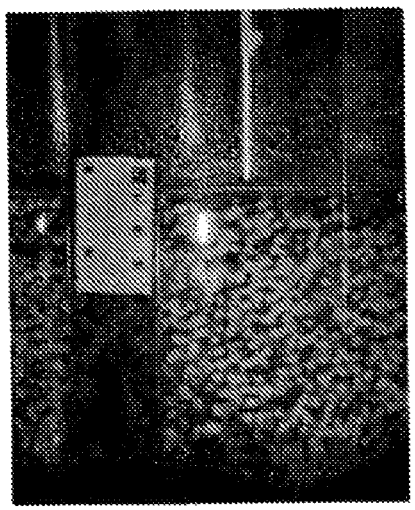
FIGS. 2A and B. A, Pellet-form mycelia of *Rhizopus oryzae* NRRL 395 in a stirred tank reactor to which rice was added; and B, cotton-like mycelia of *Rhizopus oryzae* NRRL 395 in a stirred tank reactor without added rice.
Figure 2:

The methods of the invention are based on the discovery of parameters that influence fungal pellet formation, namely 1) the use of particulate substrates; 2) duration of spore storage time and 3) inoculum size, each of which is described in detail below. Importantly, according to the methods of the invention, pellet properties such as size, density, shape, mass, etc. can be predictably controlled by the manipulation of these parameters so that an ideal morphology for particular reactor configurations, specific strains, and/or specific bioproduct applications can be achieved.

Obtaining compact pellets is important for improved reactor rheology, mass transfer, and productivity. However, up until the present invention, methods for inducing pellet formation have been developed on a case by case basis and have been extremely complex due to the many factors involved in determining pellet formation. In contrast, the methods of the present invention may be used to consistently develop compact pellets of controllable size, density (porosity) and concentration across multiple species using only simple inoculum and broth inputs. The invention thus provides simplified and efficient methods for producing compact and controllable pellets for industrial and commercial processes.

In addition, the invention also provides methods of statistically predicting the effects of varying parameters that affect fungal pellet formation and growth. In one embodiment of the invention, a logistic regression model is used to investigate (e.g. analyze and/or predict) the effects of manipulating culture conditions, variables, and interactions and to mathematically describe pellet formation for different purposes such as controlling size, density, concentration etc.

Particulate Substrates

The present invention provides methods of predictably cultivating filamentous fungi in liquid media in the form of compact, metabolically active pellets by adding particulate substrates to the liquid media. The particulate substrates serve a support for fungal mycelium growth and pellet formation. In some embodiments of the invention, the particulate substrate is a mineral substrate and may provide other advantages, e.g. by providing buffering capacity to the medium, supplying a beneficial nutrient to the fungus, etc. In other embodiments, the substrate is biodegradable and also serves as a source of nutrition for the fungus. In this embodiment, because the support particles provide nutrition for the fungus, the amount of nutrients added to the fermentation broth is minimized and simplified. Further, with pellet fermentations using biodegradable substrates, the fungal biocatalyst is more easily and efficiently removed from the broth for improved downstream separation of soluble bioproducts, and removal of the substrate is not necessary because it has been metabolized by the fungus. When mineral substrates are utilized, they too may be broken down or dissolved into the medium during incubation, leaving behind pellets which can be conveniently harvested.

In general, this embodiment of the invention involves culturing the fungi in the presence of substrate particles. When a culture medium containing substrate particles is inoculated with fungal spores and agitated, the spores tend to adhere to the particles. Upon germination of the spores, the fungal mycelia remain attached to the particles and the mycelium-particle complex develops into compact pellets as the fungus grows. When the particles also serve as a nutritive source, the need for additional additives to support fungal growth is reduced and simplified. Fungal pellets are easily maintained in liquid culture and produce high yields of bioproducts. The fungal mycelia retain the pellet morphology throughout long periods of cultivation and bioproduct formation, even though the particle portion of the pellet may be eventually metabolized. This, too, is advantageous in that there is therefore no need to separate the substrate particles from bioproducts produced by the fungus, or from the fungus itself if it is harvested for use.

The methods of the invention involve culturing fungi in liquid medium that contains particulate substrates, also referred to herein as "substrate particles", "mineral substrate particles", "biodegradable substrate particles" "biodegradable polymers", "mineral nuclei", "cereal nuclei", "nutrient particles", "nutritive particles", "polymer additives", "substrate polymers", "biodegradable polymer additives", and other similar phrases. By each of these, we mean solid, macroscopic particles that can serve as a physical support (substrate) for attachment of fungal spores and growth of the fungal mycelia, and which can be suspended in a liquid medium when the liquid medium is agitated. In some embodiments, the substrate particles are nutritive particles and can be metabolized by (i.e. serve as a food or nutrient source for, or be biodegraded by) the fungal mycelia, as the mycelium grows and increases in biomass on the particle. Examples of suitable mineral substrates include but are not limited to calcium salts (e.g. $CaCO_3$, $CaSO_4$, etc.), magnesium salts, manganese salts, and the like. In particular, $CaCO_3$, which provides pH buffer capability and serves as a surface area for spore attachment, may also be advantageously used. With respect to biodegradable substrates, a wide range of substances exist that can be successfully utilized in this manner. Preferably, such substances are natural products, or portions thereof, that exhibit a suitable size, shape and weight without extensive processing, for example, various cereals or grains (which are mostly grasses cultivated for their edible grains or fruit seeds) may be utilized, examples of which include but are not limited to rice, wheat, corn, rye, barley, millet, oats, flax seed, etc.

Such substances may be used directly without processing to adjust the size or surface area of the particles. However, the invention also encompasses the use of particles that result from some processing of nutritive sources, for example, after milling, hydrating ("cooking"), drying, pressing, crushing, etc. Examples of such processed substances include but are not limited to starch, various types of cracked corn or wheat, various cereal meals and brans (e.g. corn meal, oat bran, etc), various dried particulate soy and/or vegetable products, hulls (e.g. rice hulls) or other so-called "waste products" (e.g. agricultural waste products) that are left over after, for example, processing, etc. Such particles may be of any variety of useful shapes (e.g. spheroid, oblate, disc-like, cylindrical, chips, etc.) so long as the surface area of the particle is sufficient to allow spore adherence (agglutination), spore germination and mycelial growth. Generally, such substances will be of a size in the range of from about 10 mm or less in diameter (or in the longest dimension, in the case of non-spheroidal particles) and preferably in the range of about 6 mm, or less. However, even very fine particles (e.g. corn starch) may be utilized, and for particular applications, substrates that are on average longer than 10 mm (e.g. larger spheres, or those which are cylindrical or threadlike in shape) may also be used. Further, such particles will be of appropriate density so that they remain suspended when the liquid medium is agitated at a suitable rate, preferably without either floating on the surface or sinking to the bottom, with the understanding that heavier particles may be suspended by increasing the agitation speed of the culture. Particles of any shape, size and density may be used, so long as they serve to provide a substrate for attachment and growth of the fungus. In a preferred embodiment of the invention, the particles are rice or rice hulls, or $CaCO_3$.

In general, the concentration of substrate polymers in the medium is in the range of about 0.1 to about 20 g/L. However, preferred ranges may vary somewhat, and may be as low as about 0.01 g/L or as high as about 100 g/L, or even higher. Further, in some embodiments, a mixture of biodegradable and mineral substrates may be utilized.

Duration of Spore Storage Time: It has been discovered that spore storage time is one of the main factors influencing pellet formation. By "storage time" we mean the length of time that the spores are kept refrigerated, preferably in water at 4° C. In particular, it has been discovered that, contrary to teachings in the prior art, shorter spore storage duration (e.g. newly prepared spores) has a negative effect on pellet formation whereas increasing storage duration causes a corresponding increase in the probability of pellet formation. For example, according to the methods of the invention, spores should be stored for at least about 2 days and preferably for up to about 1.5 years or even longer. Good results are obtained with spores that are stored at least one week. Studies described herein showed that deactivation of the spores (loss of ability to germinate) was not detected in spores which were stored for up to 1.5 years.

Inoculum Size: In addition, it has been discovered that improved results in pellet formation are obtained by manipulating inoculum size (spore concentration). Generally, the interaction of hyphae is considered to be the main factor for fungal clump formation. It is believed that in the early stage of growth, the higher the inoculum size is, the more interaction the hyphae have and the higher possibility clump biomass is formed. Thus, it has been concluded by other researchers that low inoculum concentrations are beneficial for pellet production (Foster, 1939). However, the maximum inoculum size is known to vary from strain to strain (Metz et al., 1977). Most studies on pellet formation of Rhizopus strains, for example, have been conducted at relatively low concentrations (less than $10^7$ spores/L) (Byrne et al., 1989a; Byrne et al, 1989b; Znidarsic et al., 1998; Znidarsic et al., 2000). However, in contrast to previous teaching by others, the studies described herein demonstrate that high inoculum spore concentrations favor the formation of pellets. For example, for Rhizopus oryzae, spore concentrations in the broad range of from about $1\times10^7$ to about $1\times10^{10}$ spores/L, preferably in the range of from about $1\times10^8$ to about $5\times10^9$, and most preferably in the range of from about $1\times10^9$ to about $3\times10^9$ are optimal and have a high probability to form pellets. It is expected that other strains of fungi inoculated in the range of from about $1\times10^7$ to about $1\times10^{10}$ spores/L will also form pellets. By "spores/L" we mean number of spores per liter of liquid media that is inoculated with the spores.

Other Factors

Those of skill in the art will recognize that other factors may also be taken into account when culturing fungal pellets. For example, the pH of the medium can also influence pellet formation. The influence of pH on pellet formation is mainly through a change in the surface properties of the fungi (Metz et al., 1977). It has been reported that different strains have different responses to pH value (Metz et al., 1977). For these strains, the optimal pH range for pellet formation may be determined on a case by case basis by methods that are well known to those of skill in the art, or with reference to teachings in the prior art. However, for Rhizopus oryzae, the results described herein show that there were no significant differences in pellet formation over the broad pH range of from 2.5 to 7. Therefore, this strain is relatively tolerant to pH compared to some other fungal strains such as Aspergillus niger and Penicillium chrysogenum, (Galbraith et al., 1969; Pirt et al., 1959; Steel et al., 1954). In the practice of the present invention, and during the cultivation of Rhizopus oryzae, it is preferable to add a neutralizing agent to the liquid medium to prevent the pH from dropping into the low pH range of 2-3, which is not favorable for biomass accumulation for any strain (Znidarsic et al., 1998). Examples of such agents include but are not limited to calcium carbonate ($CaCO_3$), NaOH, 10% ammonia solution, KOH, $Ca(OH)_2$, CaO, etc. In a preferred embodiment of the invention, the neutralizing agent is calcium carbonate. Calcium carbonate has another advantage in that, in addition to maintaining the pH of the medium at acceptable levels, it also supplies $Ca^{2+}$ ions. Calcium ions have been recognized to induce mycelial aggregation during fungal growth, which may add some degree of benefit to the pellet formation (Jackson et al., 1993).

Those of skill in the art will recognize that many liquid media are available which are suitable for cultivation of fungal pellets according to the methods described herein. In general, the preferred medium is a carbon nutrient broth, examples of which include but are not limited to Potato Dextrose Broth (PDB), and potato hydrolysate. In a preferred embodiment of the invention, the medium is Potato Dextrose Broth (PDB). In fact, the results described herein indicate that the use of PDB, in combination with other factors, may exert a positive influence on pellet formation. In addition, the liquid media may comprise a calcium salt such as $CaCO_3$, $Ca(OH)_2$, CaO, etc.

The fungal pellets of the invention are cultured in a liquid medium that is agitated. While excessive agitation can prevent the formation of pellets, a suitable level of agitation is helpful to disperse the spores and nutritive particles after inoculation, and to maintain adequate aeration and nutrient dispersal during and after pellet formation. In general, an agitation rate in the broad range of from about 120 to about 250 rpm, and preferably in the narrower range of from about 170 to about 180 rpm, is preferred. For most cultures, an agitation rate of about 170-180 rpm is sufficient.

With respect to the temperature of fungal cultivation, the results presented herein show that temperature does not appear to affect pellet formation. However, higher temperatures do have a positive effect on fungal growth and biomass accumulation. According to the practice of the present invention, the cultivation of fungi is typically carried out at a temperature in a broad range of from about 15 to about 40° C., and preferably in a narrower range of from about 25 to about 30° C. Those of skill in the art will recognize that the optimal temperature may vary from strain to strain. The optimum temperature for growth may be determined on a case by case basis for individual fungus strains, by techniques that are familiar to those of skill in the art.

The methods of the invention thus result in the customized preparation of fungal pellets possessing several desirable traits. Among the traits that can be varied is that of the density or porosity of the pellets. The "density" or "porosity" of a pellet is represented by the ratio:

$$\phi = \frac{V_v}{V_t}$$

where $V_V$ is the volume of void-space (such as fluids) and $V_T$ is the total or bulk volume of material, including the solid and void components. Both the mathematical symbols $\phi$ and $\eta$ are used to denote porosity. Porosity is generally expressed as a fraction between 0 and 1, although it may also be represented in percent terms by multiplying the fraction by 100. In general, the pellets of the invention have a porosity in the range of from about 5% to about 30%, and preferably from about 10% to about 20%. Generally, porosity is varied by adjusting pellet size, pellet inoculum, nitrogen source in medium, etc.

Another trait that can be induced by the methods of the invention is the stage of maturation of the fungi that form the pellets. Pellets produced by most other known methods are comprised principally (e.g. >50%) of non-metabolic "bud" cells. By bud cell we mean cells which are newly developed and primarily focused on growth as opposed to secondary metabolic production as is often desired in these fermentation processes. Conversely, mature cells are those cells at such a state as to be able to actively metabolize material to desired products and secondary metabolites. By adjusting the parameters described herein, it is possible to advantageously produce fungal pellets comprised predominantly (e.g. >50%) of metabolically active "mature" cells. For example, when biodegradable nuclei are used in combination with aged spores, this leads to the presence of more mature cells. However, those of skill in the art will appreciate that for some purposes, it may be advantageous to obtain fungal pellets comprised of mostly (e.g. >50%) bud cells. This mixed growth of bud and mature cells is differentiated from many genetic engineering approaches used to induce pellet development as a majority of the cells appear to be of only a bud nature due in part to the genetic alteration that induces the pellet morphology.

As discussed herein, one advantage of the present invention is that the size and shape of the pellets that are produced can be tailored to specific needs, and to be generally uniform throughout a batch of cultured fungus. In other words, in general, the particles from a single batch of cultured fungus will have, similar dimensions and a similar three-dimensional appearance. Those of skill in the art will understand that some variability may be present. Nevertheless, by following the teachings herein, pellets of relatively uniform size and shape can be obtained. By "relatively uniform size" we mean that the majority of the pellets (e.g. at least 50%, preferably at least 60%, more preferably at least about 70%, even more preferably more than about 80%, and most preferably about 90% or more of the pellets) in a single batch of fungus are, have, on average, the same dimensions (i.e. less than about ±10% or less deviation from the average). In general, a preferred shape is substantially "round" ("spherical" or "spheroidal"). However, other shapes may also be obtained, e.g. the shape may be generally or substantially elliptical, ovoid, disc-like, cylindrical, threadlike, etc. In general, a preferred size of the pellets is in the range of from about 1 mm to about 10 mm, and preferably about 2-5 mm in the longest dimension (e.g. diameter if a sphere or disc; major axis if elliptical or ovoid; length if cylindrical or thread-like; etc.). Control over pellet size and shape is the result of manipulating factors such as substrate concentration, spore inoculum concentration, pH control (e.g. by $CaCO_3$), shaking speed, polymer addition etc.

The methods of the invention may be utilized to culture a wide variety of filamentous fungi in pellet form. Examples of fungi that may be cultivated by these methods include but are not limited to various *Rhizopus* species (e.g. *Rhizopus oryzae* as in ATCC deposits 20344, 10260 and 9363) and other members of the Zygomycota phylum; various *Trichoderma* species (e.g. *Trichoderma reesei* as in ATCC deposit 56765); various *Aspergillus* species (e.g. *Aspergillus niger*; *Aspergillus phoenicis* as in ATCC deposit 52007; *Aspergillus terreus* as in ATCC deposit 20542) and other members of the Asconycota phylum; various *Phanerochaete* species (e.g. *Phanerochaete chrysosposium*), etc. Those of skill in the art will recognize that the present invention provides a general pelletization method for most if not all filamentous fungi.

The fungal pellet cultivation methods of the invention are especially well-suited to the commercial preparation of bioproducts that are produced by the fungus. The bioproducts are typically fungal fermentation products, and may be, for example, secondary metabolites. Such bioproducts include but are not limited to organic acids (e.g. lactic acid, especially optically pure L-(+) lactic acid; fumaric acid; etc.); enzymes (e.g. ligninases and cellulases which are used for the production of ethanol from lignocellulosic materials); antibiotics (e.g. penicillin); various drugs (e.g. cholesterol lowering statins such a lovastatin; etc.

In addition, the fungal mass itself may serve as a rich source of chitin and chitin derivatives, and the methods of the present invention, which result in a high biomass accumulation, are well-suited to facilitate the production of chitin and chitin derivatives. Chitin derivatives include, for example, chitosan, various sulfated and acetylated chitins and chitosans, chitin derived oligosaccharides, glucosamine, etc.

Use of a Multiple Logistic Regression Model

As described above, by inoculating the fungus into a liquid culture medium containing biodegradable polymers, and (optionally) by manipulating one or more of the parameters discussed herein, pellet formation of a particular size, density and concentration can be attained. As an additional contribution to the art, the present invention also encompasses the use of statistical methods to determine, in advance, the probable effect on pellet formation of altering one or more parameters. In particular, the present invention encompasses the use of a multiple logistic regression model in this respect. This statistical model has been used to describe the probability of the occurrence of an event in fields such as economics, environmental studies and microbiology (Neter, 1996; Skierve,1992; Lopez-Malo, 2000). However, according to the present invention, the model has been adapted to predict the probability of the occurrence of pellet formation using the parameters discussed herein as predictor variables. In the logistic model, the response Y of the logistic model is usually binary, defined to have the two possible outcomes: occurrence and without occurrence. As applied to the present invention, the response variable Y is defined as the two possible outcomes of pellet formation: forming pellets or not forming pellets (coded 1 and 0, respectively). Such predictions can be tailored to specific species and/or to a particular size, density and concentration of pellet.

The invention may be further understood in view of the ensuing examples, which serve to illustrate the invention but are not intended to limit its scope in any way.

EXAMPLES

Example 1

Pelletization of Rhizopus oryzae

Materials and Methods

R. oryzae NRRL 395 (ATCC 9363) obtained from the American Type Culture Collection (Manassas, Va.) was first cultured on potato dextrose agar (Difco) slants to form spores. The culture temperature was 25° C. The spores were washed from the agar with sterile distilled water. Various seed media were prepared with potato dextrose broth, (PDB), (Difco, 254920), $CaCO_3$ and with or without 20 g/L rice as a biodegradable polymer. Specifically, the cultures without biodegradable polymer contained 12 g/L of PDB and an inoculum spore concentration of $1 \times 10^8$ spore/L was used. For the cultures that contained a biodegradable polymer, 48 g/L of PDB and an inoculum spore concentration of $3 \times 10^9$ spore/L was used. Each spore solution was inoculated into a 125 mL Erlenmeyer flask, containing 50 mL seed medium. The cultures were agitated at 27° C. for 48 hours on an orbital shaker bath (Lab-line Shaker, Model: 3540, Melrose Park, Ill., U.S.A.) at 170 rpm.

Results

The results are presented in FIGS. 1A and B. FIG. 1A shows that, in the absence of a biodegradable polymer, the fungus grew as clumps. In contrast, fungus grown in the presence of a biodegradable polymer (rice) exhibited a very different morphology. This is illustrated in FIG. 1B, which shows the fungus pellets that formed in the presence of the biodegradable polymer.

Table 1 shows a comparison of lactic acid production using various commercial techniques and the pellet-induced and non-induced strategies. The FIG. 1 and Table 1 together show the significant affect the pelletization strategy has on increasing lactic acid production in terms of yield, concentration in broth, and productivity. Also, the biodegradable support used in the pelletization can be used as a nutrient for fungal growth, resulting in no extra separation costs.

TABLE 1

Comparison of Different Fungal Fermentations

| Fermentation | Lactate (g/L) | Yield (%) | Product. (g/L · h) |
| --- | --- | --- | --- |
| Immobilized cells[a] | 62~73 | 64.8~72 | 1.6~26 |
| Non-pellet | 33 | 36 | 0.45 |
| Pellet (batch culture) | 72 | 71 | 3 |
| Pellet (fed batch culture) | 138 | 86 | 1.4 |
| Pellet (repeated culture) | 72 | 86 | 2.8 |

[a]Vaidyanathan et al., 2000

Although this example is with a particular strain of R. oryzae, the same results have been shown to be possible in multiple other fungal strains (data not shown).

Example 2

Production of Ligninases by Phanerochaete chrysosposium in Pellet Form

White rot fungus Phanerochaete chrysosposium is a well known filamentous fungus that can deconstruct lignocellulosic materials by excreting extracellular oxidative enzymes (ligninases), such as lignin peroxidase and manganese peroxidase. As a filamentous fungus, the morphology of P. chrysosposium in liquid culture can be either clump (mat)-type or pellet-type. The clump morphology increases the viscosity of the medium, wraps around baffles and impellers which influence the nutrient mass transfer and reactor performance. The situation would be more significant for ligninase production using P. chrysosposium because ligninase synthesis needs high $O_2$ tension and low shear stress (Kirk, et al., 1990). Using pelletized fungi can solve these problems. Pelletization of filamentous fungi makes it possible not only to improve the nutrients mass transfer, but also to increase significantly oxygen concentration and to reduce the shear stress. Consequently, the pelletization technology enhances the reactor performance by increasing ligninolytic enzyme productivity. In this Example, ligninase production from clump morphology and pellet morphology induced by the methods of the present invention are first compared. The effects of biomass concentration, minimal oxygen tension, agitation, and medium composition on ligninase production are then presented.

Materials and Methods

Flask cultures with pellet and mat P. chrysosposium were performed at 39° C., 200 rpm using chemical defined medium (Tien and Kirk, 1988). One unit of manganese peroxidase (MnP) activity was defined as the activity of an enzyme that catalyzes the conversion of 1 μmole of guaiacol per minute. For some experiments, glucose, ammonium tartrate, trace elements and $CaCO_3$ were added as indicated.

Results

Figure 3A:
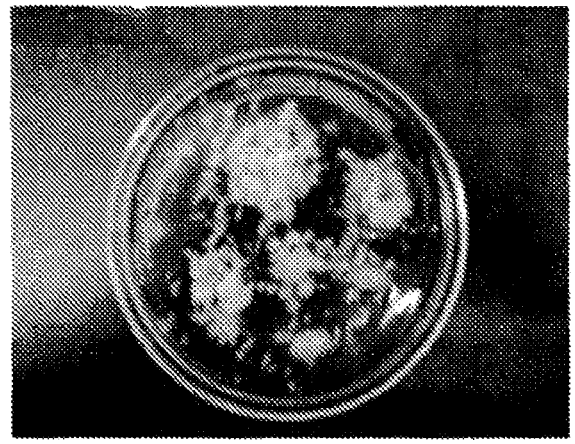
FIGS. 3A and B. *P. chrysosposium* grown in A, clump and B, pellet form.
Figure 3B:
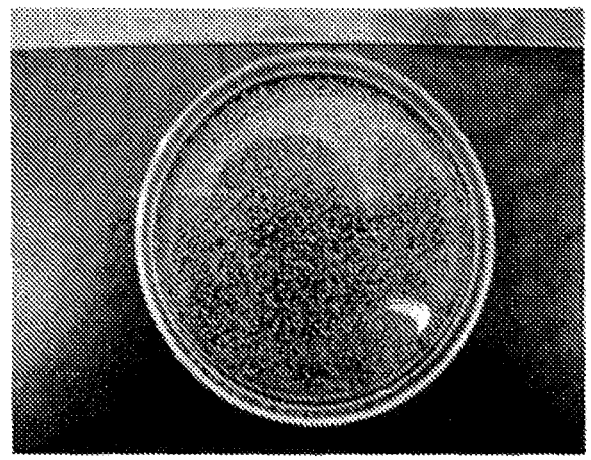
Figure 4A:
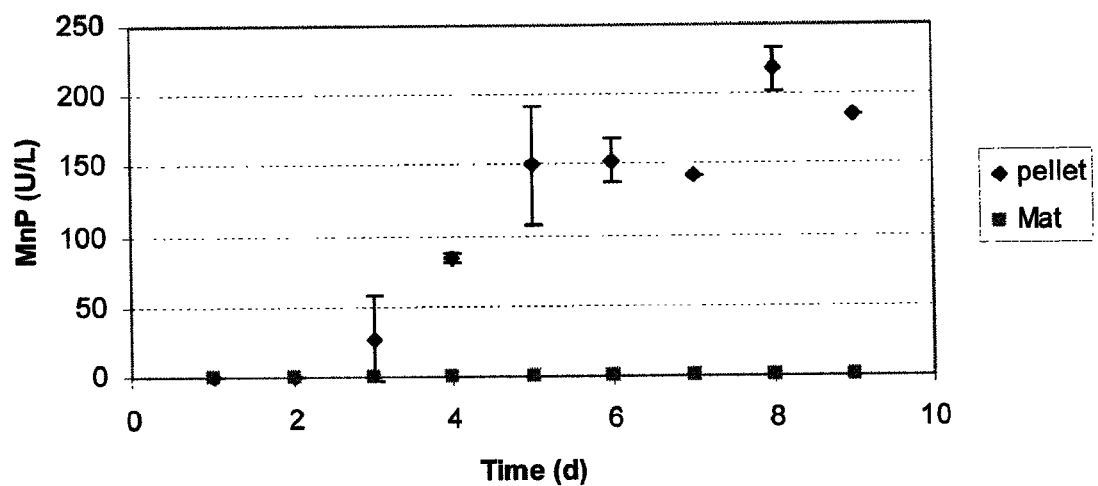
FIGS. 4A and B. A, effect of morphology on manganese peroxidase (MnP) production; B, effect of morphology on biomass production.
Figure 4B:
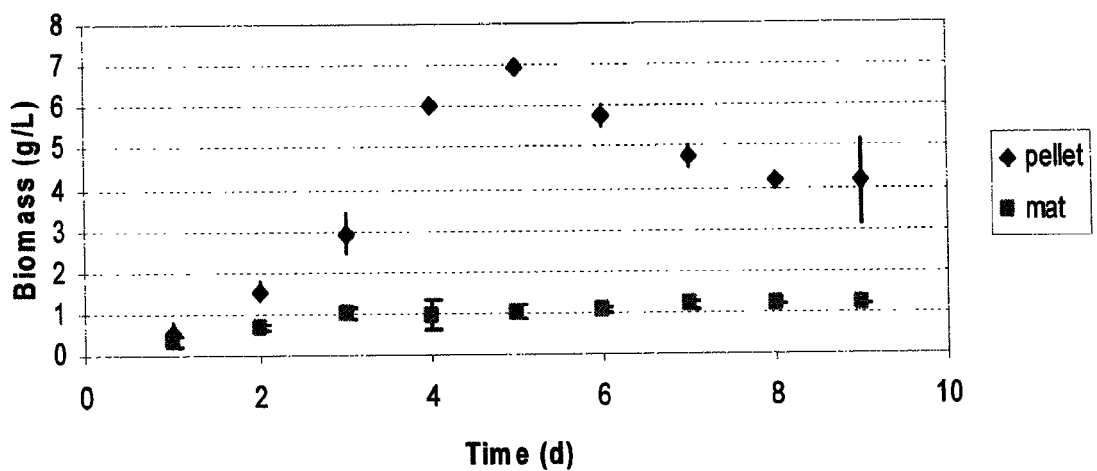

FIGS. 3A and B show the morphology of P. chrysosposium grown in clump form (FIG. 3A) and as pellets (FIG. 3B). The effect of these different morphologies on manganese peroxidase and biomass production is illustrated in FIGS. 4A and B.

As can be seen, manganese peroxidase and biomass production were both significantly greater in the fungal pellet culture. Thus, a pelletized morphology of *P. chrysosposium* in liquid culture significantly increased the production of the ligninase manganese peroxidase, in comparison to production of the enzyme in a clump-like culture.

Example 3

Co-production of Lactic Acid, Chitin and Chitin Derivatives Using Pelletized *Rhizopus oryzae*

Lactic acid ($CH_3CHOHCOOH$) is a colorless compound that is important in both international and domestic markets for several industries. Lactic acid is widely used as an acidulant and flavoring and preservative in the food industry. There is also an increased interest in its application in the production of poly-lactic acid, which can be used for biodegradable plastics. Both the polymers and co-polymers derived from lactic acid are especially attractive for biomedical application because of their biocompatibility, body absorption and blood compatibility. The increased use of lactic acid in existing applications and its potential in biodegradable plastics has made producing lactic acid an attractive investment.

Lactic acid can be produced by both bacteria and fungi fermentation. Presently the majority of fermentation processes utilize bacterial strains that produce non-optically pure lactic acid product which requires a somewhat complex growth media that adds cost to the process and has shown to have negative effects on the downstream processing of the polymer (Blomquist, 2001; Zhou et al., 2003; Tsuji, 2002). In contrast, the fungus *Rhizopus oryzae* NRRL 395 has been proven to be a good lactic acid producer and has several advantages compared with bacterial fermentation. These include: (1) higher tolerance to low pH environments; (2) the fungal biomass is relatively easy to separate from the broth, and thus, facilitates downstream processing, (3) the fungus only produces enantiopure homochiral L-(+) lactic acid, and (4) *Rhizopus* fungi have lower nutrition requirements which can reduce the fermentation cost and simplify the downstream product separation process (Magnuson et al., 2004; Tsao et al., 1999).

When lactic acid is produced using the fungal strain *Rhizopus oryzae*, a considerable amount of fungal biomass, whose cellular wall is primarily composed of chitin, was concurrently produced. Chitin is a polysaccharide, and is speculated to be the second most abundant biopolymer in the biosphere. The structure of chitin is a linear polysaccharide made up of β-(1,4)-2-acetamido-2-deoxy-D-glucopyranosyl units where each individual residue is N-acetyl-D-glucosamine (Khor, 2001). The structural characters of chitin make it a useful biopolymer for use as a coagulating agent in water treatment, a plant seed coating agent in agriculture, and a biomedical bio-absorbent (Yusof et al., 2001). Chitin is widely distributed in the animal and plant kingdom, such as in the shells of crustaceans and mollusks, algae, and fungi (Muzzarelli, 1985). Khor (2001) has estimated that the annual world market for chitin is at $1.9 billion while the sub-market for biomedical chitin is $1.25 billion. Traditionally, chitin is commercially produced from animal sources such as shellfish and crab, which has some economic liabilities resulting from the use of a non-renewable source and limitation on biomedical usage due to residual proteins, trace minerals and metals that have side effects such as allergic reactions (Khor, 2001). Producing chitin from fungi can avoid such problems. Moreover, the chitin content of fungi can be as high as 10% to 90% (Carlile, 2001).

There is an inherent challenge in the fermentative organic acid production with filamentous fungi. The fungi tend to form cotton-like mycelia which limited the mass transfer of oxygen and nutrients onto the microorganisms and the release of the produced organic acids into bulk solutions. These factors ultimately lead to a low yield and productivity of organic acids in fungi fermentation. Growing fungi in pellet form can alleviate these problems.

It has been reported that the growth and metabolism of *Rhizopus oryzae* is limited by nitrogen (Foster et al., 1939; Rhodes et al., 1959; Rhodes et al., 1962). Too much nitrogen in the broth leads to a faster fungal growth than organic acid production. Therefore, in terms of improving fermentation performance, the lactic acid fermentation processes can be divided into three steps: 1) pelletized seed culture; 2) fungal biomass cultivation with nitrogen; and 3) lactic acid production with less nitrogen or no nitrogen (Kenealy et al., 1986; Zhou et al., 2002; Romano et al., 1967). The process of lactic acid production provides a possibility to simultaneously produce lactic acid and chitin using potato hydrolysate and glucose. For example potato hydrolysate contains 100 g/L glucose and 10 g/L crude protein, which represents not only a carbon source but also a good nitrogen source for microorganisms. This means that potato hydrolysate can be used as a nitrogen source to grow fungal biomass and for chitin accumulation. Then the fungal biomass is transferred to a sole carbon source (glucose) broth to produce lactic acid.

This Example describes the development of a novel process of lactic acid and chitin co-production using pelletized *Rhizopus oryzae* NRRL 395 to improve both fermentation yield and productivity on potato hydrolysate and glucose as nutrient sources. The specific objectives were to: (1) determine the influence of nitrogen and carbon concentration on lactic acid production and chitin content in biomass, (2) investigate the influence of potato hydrolysate on lactic acid and biomass production in cultivation process, and (3) enhance the lactic acid production by increasing the biomass concentration, depriving nitrogen source in the broth of batch, repeated batch, and fed-batch fermentations.

Materials and Preparation

Three kilograms of fresh cull potatoes were boiled and mashed before adding 0.3% α-amylase (A7595-250 ml, Sigma_Aldrich Corp., St. Louis, Mo.) to liquefy the starch at 75° C. for one hour. Then 0.1% glucoamylase (A7255-100G, Sigma-Aldrich Corp., St. Louis, Mo.) was added and reacted at 55° C. until the reducing sugar content of hydrolysate (detected by the 3,5-Dinitrosalicylic acid (DNS) method) no longer increased within two hours. After solid and liquid separation, the liquid hydrolysate was used to prepare a cultivation medium. The liquid hydrolysate contained 100±20 g/L of glucose and 9.4±1.0 g/L of crude protein.

Microorganism and Spore Culture Method

The fungus *Rhizopus oryzae* NRRL 395 was obtained from the American Type Culture Collection (Manassas, Va.). The fungus was first grown on potato-dextrose agar (PDA) (Difco, 213400, Sparks, Md.) slants at 30° C. for 7 days. For experimentation, the fungal spores in the slant were suspended in sterilized water maintained at 4° C. For storage, the spores were placed in a 20% glycerol solution at −80° C. Pelletized seed was cultured on the medium with 24 g/L potato dextrose broth (PDB) (Difco, 254920, Sparks, Md.) mixed with 6 g/L $CaCO_3$. In terms of achieving pellet form, the spore solution was inoculated in a 125 ml Erlenmeyer flask, containing 50 ml of seed medium with a spore concentration of $1 \times 10^6$ spore/ml, and cultured at 27° C. on a orbital shaker bath (Lab-line Shaker, Model: 3540, Melrose Park, Ill., U.S.A.) set at 170 rpm for one day. The culture temperature was fixed at 27° C. The spore storage time was 90 days. The resulting broth was used as the pellet seed for the ensuing experiments. The diameter of seed pellet was 1.13±0.22 mm.

Biomass Cultivation

A Completely Randomized Design (CRD) with three replicates of six cultures was used to study the effects of the potato hydrolystate content on fungal biomass and chitin during cultivation. Six potato hydrolysate contents (0, 10, 25, 50, 75, 100%) were studied. For each individual potato hydrolysate content medium, additional glucose was added making the total glucose concentration 120 g/L. Calcium carbonate was used to keep the pH at 5. The inoculum for all cultures was fixed at 0.12 g dry pellet biomass/L. The cultures were processed for 2 days in 250 ml flasks containing 100 ml medium at 27° C. using an orbital shaker (Classic Series C24 Incubator shaker, New Brunswick Scientific, Edison, N.J., U.S.A.) at 170 rpm.

Lactic Acid Production

Two replicates of five cultivated biomass concentrations (1.73, 4.09, 6.47, 13.90, and 17.30 g dry biomass/L) were inoculated onto the media which contained only 100 g/L of glucose. Calcium carbonate (35 g/L) was added as the neutralizer to maintain the pH around 5.5. The cultures were processed for 2 to 4 days in 250 ml flasks containing 100 ml medium at 27° C. using an orbital shaker (Classic Series C24 Incubator shaker, New Brunswick Scientific, Edison, N.J.) at 170 rpm.

Repeated Batch Fermentation

The initial culture conditions were the same as described in the previous section. The inoculum size was 13.7 g/L pelletized fungal biomass. The cultures were processed in 1000 ml flasks containing 300 ml of the medium. The strategy of repeated batch culture was: using the same fungal biomass, separating the product solution and adding the fresh culture medium for each subsequent batch. Two replicates were carried out for this experiment. The initial glucose concentration for the first batch was 80 g/L, and the inoculum was 13.7 g/L pelletized biomass. At the end of each batch, the pellet fungal biomass was sterilely separated from the medium solution by a No. 40 standard screen; and then a 300 ml fresh medium solution with a sole carbon source of 100 g/L glucose was added to the flask to create the next batch of culture.

Fed Batch Culture

The pelletized fungal biomass was cultured using the same method as described in previous section. The biomass of 13.9 g/L was inoculated into 1 L fermentor (Bioflo 110 Modular Benchtop Fermentor, New Brunswick Scientific, N.J.) containing 300 ml production medium that included 100 g/L glucose and 35 g/L $CaCO_3$. The fermentation was carried out at 27° C. with 200 rpm agitation speed and 1 volume per volume per minute (vvm) aeration rate. An extra 100 mL medium with a glucose concentration of 600 g/L was fed into the fermentation after 30 hours. During the stage of fed-batch fermentation, sodium hydroxide solution (25% NaOH), instead of calcium carbonate, was used as the buffer to maintain the broth pH at 5.0.

Statistical Analysis

A pair wise comparison using the Statistical Analysis System program 8.0 (SAS Institute Inc. NC) was conducted to identify the effects of potato hydrolysate on fungal biomass and chitin content during cultivation. The effects of pellet biomass concentration and repeated batch fermentation on lactic acid production were analyzed using the pair wise comparison as well.

Analytical Methods

Lactate in the broth was analyzed using a Dionex DX-500 system (Sunnyvale, Calif.) (Liu, 2005). Dry biomass was determined by washing the pellet mycelia with 6N HCl and then washing to pH 6 with deionized distilled water. The washed biomass was dried at 100° C. overnight before weighing. The diameter of seed pellets was determined using an Olympus microphotograph system (Tokyo, Japan).

N-Acetyl-D-glucosamine (NAG), as the major component of chitin, was used to express the total amount of chitin in the biomass. A modified analysis method of hydrochloric acid hydrolysis (Muzzarelli et al., 1985) was used. A 0.25 g dry biomass mixed with 25 ml of 6 N HCl solution was hydrolyzed at 100° C. for 4 hours. The hydrolysate was neutralized by 1 N NaOH to a pH of around 5, and the NAG concentration in the hydrolysate was measured using a Dionex DX-500 system coupled with a CarboPac PA 10 guard (4×50 mm) and analytical (4×250 mm) columns and a ED40 detector (Sunnyvale, Calif.). The running eluent was 18 mmol NaOH, and the washing eluent was 200 mmol NaOH.

Results and Discussion

Figure 5A:
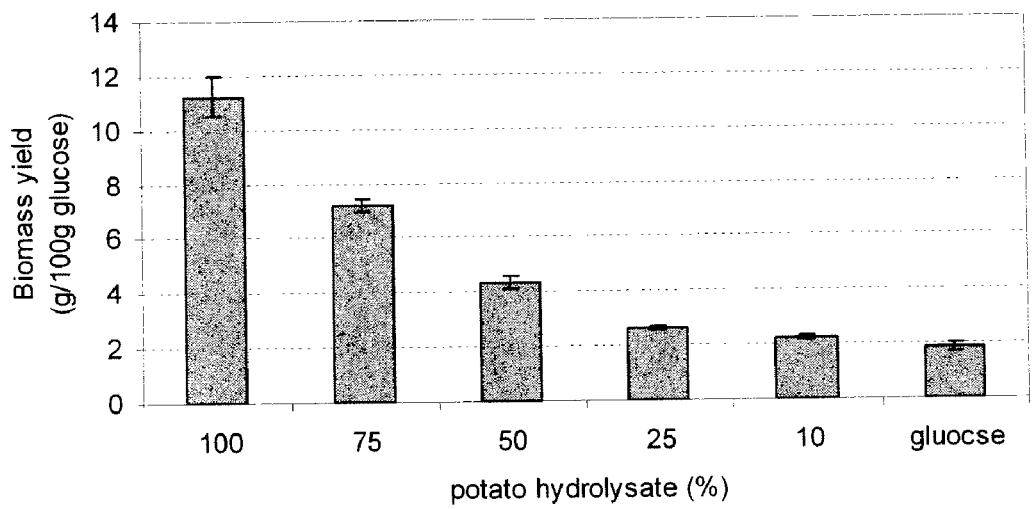
FIGS. 5A and B. Effects of potato hydrolysate on A, biomass production and B, lactic acid production during cultivation. Data are presented as the mean of three replicates with standard deviation.
Figure 5B:
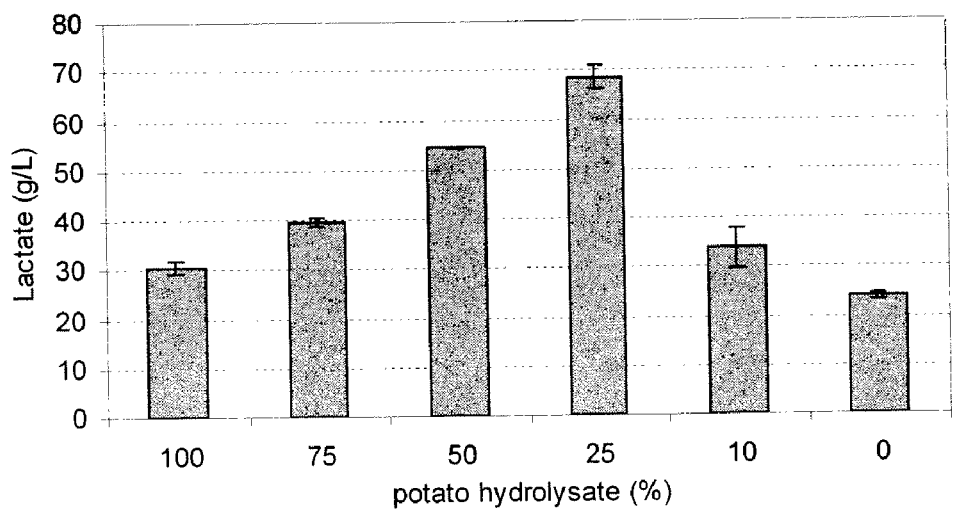

Different percentages of potato hydrolysate had significant ($P<0.05$) influence on fungal biomass cultivation (FIG. 5A). The data show that both total biomass and chitin content decreased following a decrease in the percentage of potato hydrolysate (FIG. 5A, Table 2). The cultivation on 100% potato hydrolysate had the highest fungal biomass at 11 g/L with respect to the highest chitin content of 0.25 g/g biomass (Table 2) and a lactate concentration of 30 g/L (FIG. 5B). It has been reported that nitrogen had a positive effect on chitin accumulation during fungal growth (Arcidiacono et al., 1992.) Since the potato hydrolysate contained 9.4 g/L of protein, most of it being proteins and amino acids, which can be well utilized by the fungus to increase both biomass and chitin content. Thus, the higher the protein concentration was in the medium, the more biomass and chitin produced from the culture.

TABLE 2

Chitin contents in biomass from cultures on different percentage of potato hydrolysate[a]

| Potato hydrolysate content (%) | Chitin content, g/g biomass |
|---|---|
| 100 | 0.25 ± 0.05 |
| 50 | 0.14 ± 0.03 |
| 25 | 0.10 ± 0.02 |
| 10 | 0.07 ± 0.03 |

[a]Data are the average of triplicates with standard deviations (n = 3)

In addition, the lactate concentrations obtained from the cultures and produced from the different percentages of potato hydrolysate, demonstrate the effects of potato hydrolysate on lactate production during the cultivation. The lactate concentration first increased following a decrease in the percentage of potato hydrolysate. It reached the highest value of 69 g/L in three days culture at the 25% of potato hydolysate. Then the lactate concentration leveled off following the further decrease of the percentage of potato hydrolysate. This indicates that protein influenced the lactate production by controlling the biomass growth. A large amount of protein in the medium was favorable to biomass growth but correspondingly it inhibited the lactate production, while less protein content leads to less biomass growth which also caused the reduction of lactate production. Thus, in terms of cultivation which is to produce more chitin with less or no lactate production, 100% potato hydrolysate was chosen for fungal biomass cultivation. At the 100% potato hydrolysate concentration, the cultivation produced 11 g/L of fungal biomass and 0.25 g/g of chitin along with 6000 pellets/L with an average pellet diameter of 2.9 mm.

Figure 6A:
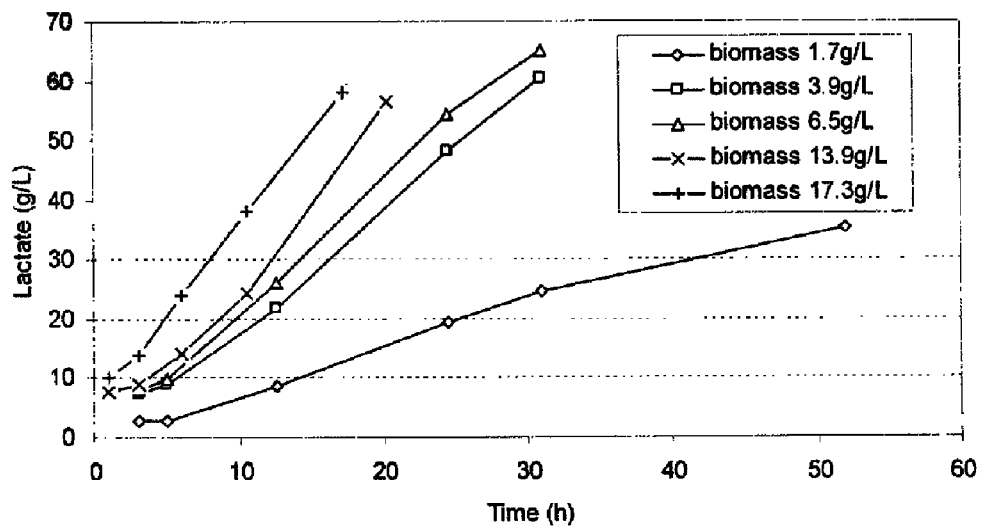
FIGS. 6A and B. Effects of fungal biomass on lactic acid A, production and B, productivity. Data are presented as the mean of two replicates.
Figure 6B:
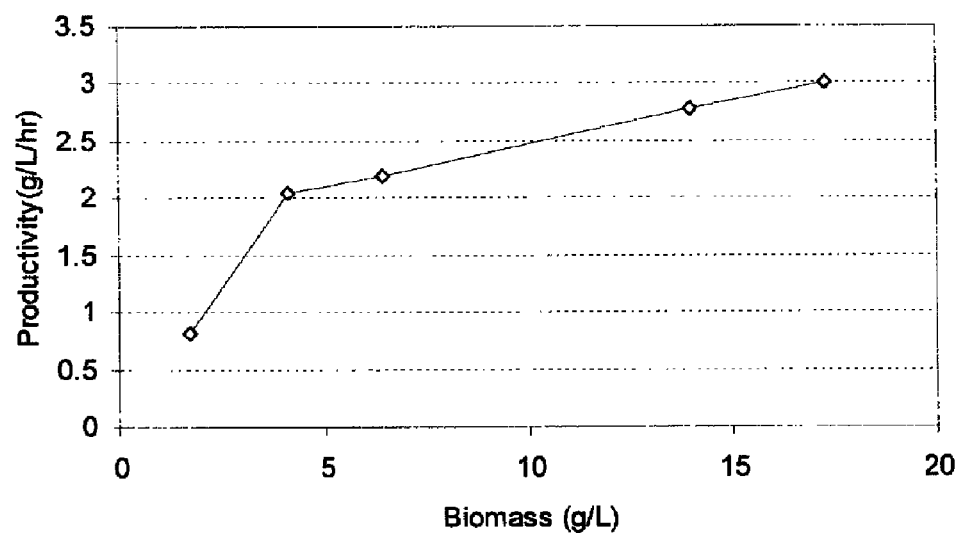

Lactic Acid Production: Effects of Biomass Concentration on Lactic Acid Production FIG. 6A shows that in the lactic acid production step, the lactate concentration varied with different biomass concentrations. Lactate production increased following the increase of initial biomass concentration. Lactate concentration reached 58 g/L at an initial biomass concentration of 17.3 g/L in 17 hours of culture, which is much higher than the 35 g/L concentration obtained with an initial biomass concentration of 1.7 g/L in 52 hours (FIG. 6A). Meanwhile, the data for lactic acid productivity further demonstrate that the production rapidly increased from 0.8 g/L/h to 2 g/L/h as biomass concentration increased from 1.7 g/L to 3.9 g/L (FIG. 6B), and then production further increased following the increase of biomass concentration (FIG. 6B). It reached 3 g/L/hr when the biomass concentration was increased to 17.3 g/L. In addition, the data also shows that the fungal biomass had no significant growth without a nitrogen source during the lactic acid production step (Table 3).

TABLE 3

Comparison of biomass during lactic acid production[a]

| | Initial biomass concentration inoculated for lactic acid production (g/L) | Biomass concentration after lactic acid production (g/L) |
|---|---|---|
| Culture 1 | 1.71 | 1.82 |
| Culture 2 | 3.90 | 4.12 |
| Culture 3 | 6.55 | 6.63 |
| Culture 4 | 13.92 | 14.79 |
| Culture 5 | 17.37 | 17.85 |

[a]data are the mean value of two replicates

These results demonstrate that the maintenance of fungal metabolism does not require a nitrogen source and that lactic acid production is mainly influenced by the total amount of fungal biomass in the broth. Thus, in terms of both lactate productivity and final lactic acid concentration, the data indicate that the more pelletized fungal biomass was inoculated in the culture, the higher lactate productivity and concentration could be reached. However, the high biomass concentration means a high pellet density, which could cause problems with mass and oxygen transfer and further make it difficult to maintain the high lactate productivity and increased lactic acid production. Thus, in this study, the pelletized fungal biomass of 13.9 g/L was selected as the operational inoculum for the next step in lactic acid production.

Lactic Acid Production with Repeated Batch Culture

Developing an efficient lactic acid production system was one of targets of this study. Pellet morphology makes it possible to perform repeated batch culture to enhance fermentation efficiency. Meanwhile, repeated batch culture has the advantages of high productivity and a low possibility of contamination as well (Yin et al., 1998). In this system, fermentation broth was pumped out at the end of each batch, and then fresh medium was added to the fermentor to begin the next batch. This was repeated continuously until lactic acid production began to decrease significantly. Lactic acid can be separated from the broth and chitin can be extracted from fungal biomass. Therefore, high yield/productivity of lactic acid and chitin can be achieved.

Figure 7A:
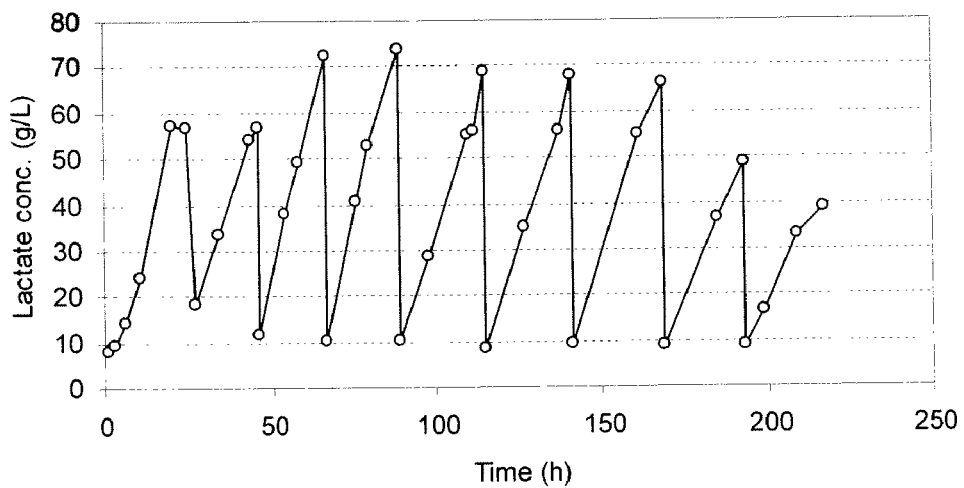
FIGS. 7A and B. Repeated batch fermentation of lactic acid production. A, lactate; B, glucose. Data are presented as the mean of two replicates.
Figure 7B:
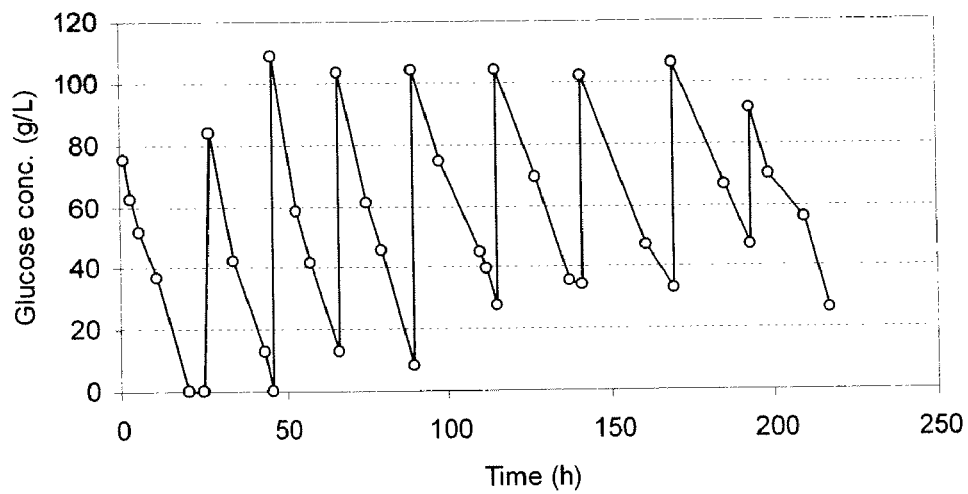
Figure 8A:
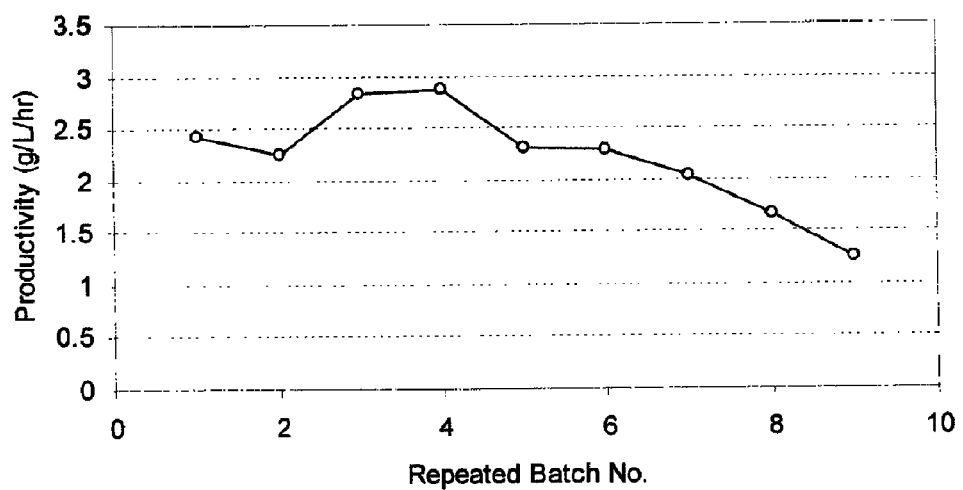
FIGS. 8A and B. A, productivity and B, lactate yield of each batch during repeated batch fermentation. Data are presented as the mean of two replicates FIG. 9. Lactic acid production using fed batch culture of *R. oryzae* NRRL 395 in a 1 L-stirred tank fermentor. The aeration rate and agitation speed were 1 vvm and 200 rpm, respectively. The pH was adjusted at 5.0±0.1 with $CaCO_3$ and 25% NaOH. 13.9 g/L pelletized biomass seed was inoculated into fermentor and cultured at 27° C. for 100 hours. 100 mL fed-medium with 60 g glucose was added at the 30th hour.
Figure 8B:
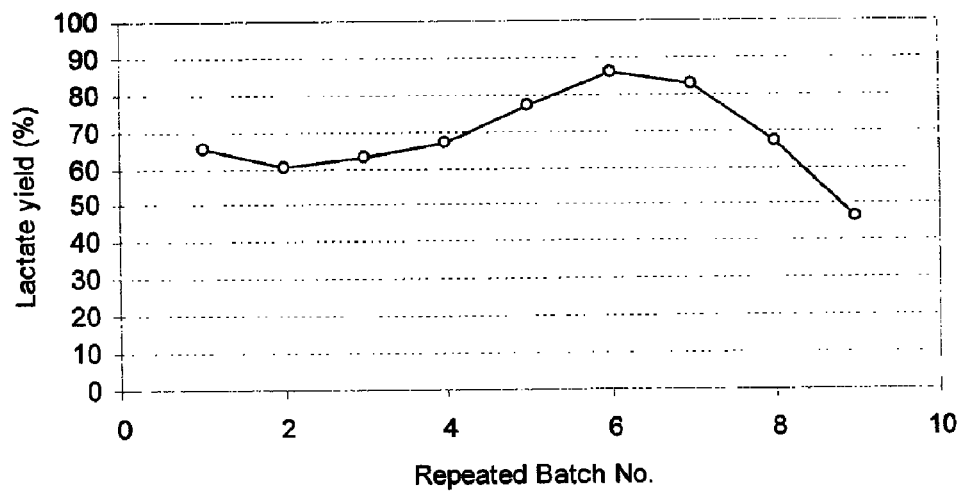

FIGS. 7A and B show the fluctuations of lactate (A) and glucose (B) during fermentation over nine repeated batches. The lactate concentration increased following the increase of repeated batches at the first 3 batches (FIG. 7A). The average lactate concentration of batch 3-6 was 70 g/L. The statistical analysis of pair wise comparison demonstrated that there were no significant (P>0.05) differences in lactate concentration from batch 3 to batch 6. After the sixth batch, the lactate concentration rapidly decreased during the last three batches. The lactate generated from the ninth batch was only 40 g/L. The effects of repeated batches on the productivity and lactate yield are illustrated in FIGS. 8A and B. Lactate production during the first 7 batches was higher than 2.0 g/L/h. The trend of productivity during the repeated batch fermentation was: the lactate productivity slightly, but significantly (P<0.05), increased in the first 3 batches; it reached the highest productivity of 2.9 g/L/h at batch 4; and then the productivity decreased in subsequent batches; at batch 9 the productivity dropped to 1.2 g/L/h. The lactate yields during the repeated batch fermentation present a similar trend. The only difference is that the lactate yield kept increasing in the first 6 batches and then leveled off. The highest yield (86%) was achieved at batch 6.

In addition, the pellet size and the biomass concentration from repeated batch cultures with a sole carbon source did not significantly (P>0.05) change during the entire fermentation course (Data not shown). It has been reported that the size and concentration of fungal pellets from cultures in medium containing both nitrogen and carbon sources increased from one batch to the next. This leads to a high density of large fungal pellets which makes mass and oxygen transfer more and more difficult once the repeated batch fermentation progressed, eventually influencing the fermentation performance (Yin et al., 1997). The aeration and agitation have to be adjusted with respect to the fermentation process in order to maintain proper mass and oxygen transfer. Compared to that, the fungal biomass, with uniform pellet size and concentration during the entire course of lactic acid production, apparently had much better mass and oxygen transfer efficiency.

The results indicate that not only the pelletized fungus is able to utilize the glucose as a sole carbon source to produce lactic acid, but also the fermentation process with a sole carbon source is much easier and simpler to be operated. The data show that the first seven batches of fermentation had average values of 66 g/L of lactate concentration, 71% of lactate yield, and 2.4 g/L/h of productivity.

Lactic Acid Production with Fed Batch Culture

Figure 9:
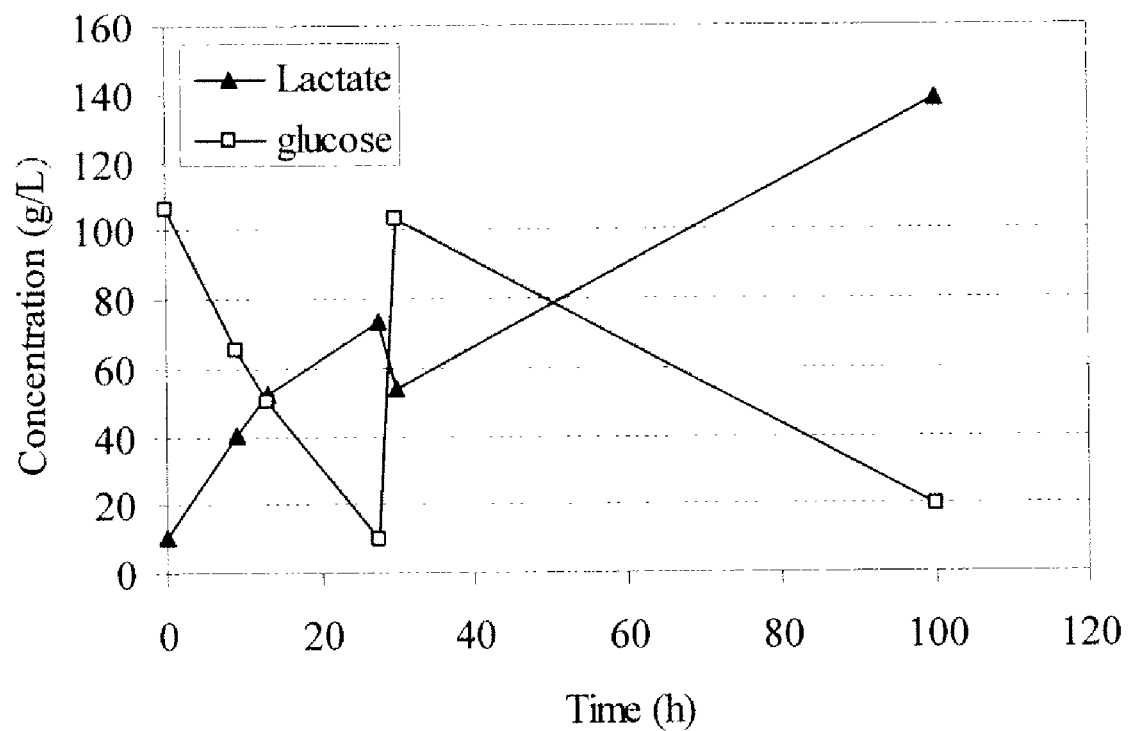
Figure 10:
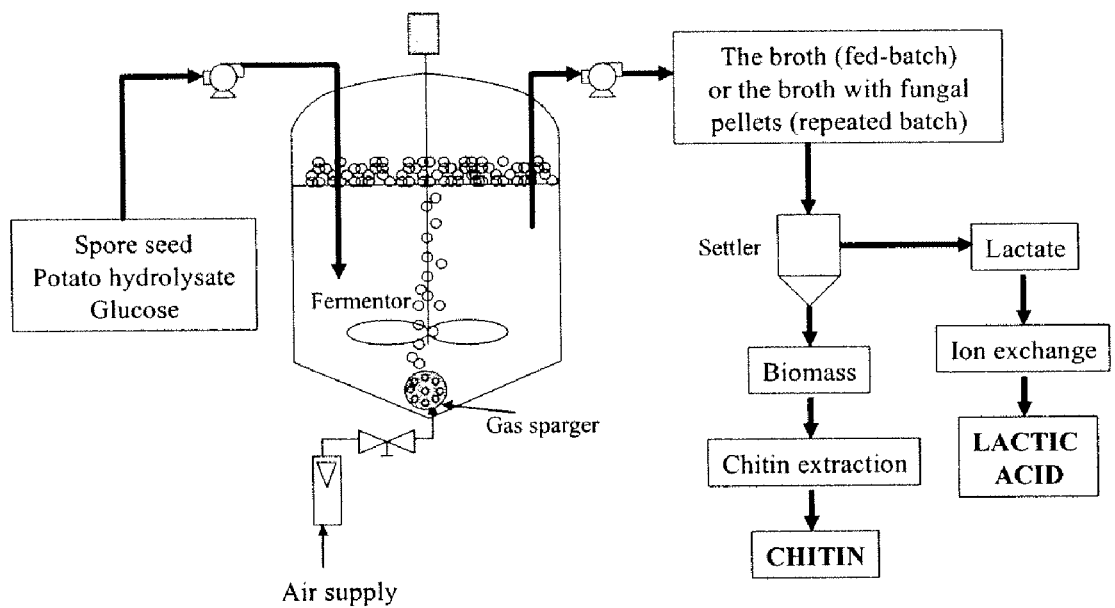
FIG. 10. Flowchart of the integrated process of co-production of chitin and lactic acid.

High concentrations of lactate in the broth was the other target of this study since a high concentration of final product is favorable for the downstream separation and can significantly reduce the operation cost of the separation. However, although it can effectively improve productivity, repeated batch culture exhibits limitations on the increase of final lactate concentration. This can be improved by the use of fed batch culture. The changes of lactate concentration and glucose concentration during the fed batch culture are shown in FIG. 9. The final lactate concentration reached at 138 g/L in a reaction duration of 100 hours with an overall yield about 86%. A higher productivity of 2.8 g/L/h was observed in the culture time of the first 28 hours, while the productivity was decreased to 0.9 g/L/h once the fresh medium was fed. The average productivity of whole process was 1.4 g/L.h. Compared to the previous study of fed batch lactic acid production from low biomass concentration (2 g/L) (Liu et al., 2006), the productivity was doubled and the yield and concentration increased 50% and 43%, respectively. The results further indicate that the higher concentration of pelletized biomass was an important step in lactic acid production no matter what fermentation process was adopted. In addition, since the lactate concentration from fed batch culture reached a very high level, and the solubility of calcium lactate is around 70 g/L, in order to avoid the formation of crystal calcium lactate, sodium hydroxide, instead of calcium carbonate, was used to neutralize the broth once lactate concentration reached 65 g/L.

This research developed a new three-step process for lactic acid and chitin co-production using pelletized *Rhizopus oryzae* NRRL 395 with potato hydrolysate and glucose as the nutrient sources. Separation of the biomass cultivation and the lactic acid production not only improved lactic acid production yield and productivity, but also enhanced chitin content. Cull potato hydrolysate used as a nutrient source for biomass cultivation can significantly increase both biomass yield and chitin content. The biomass concentration and chitin content from the culture in 100% potato hydrolysate reached 11 g/100 g glucose and 0.25 g/g biomass, respectively. Meanwhile, different fermentation methods had different influences on lactic acid production. The comparison of three different cultures to produce lactic acid concluded that: (1) lactic acid production was significantly enhanced by increasing biomass concentration, removing the nitrogen source in the fermentation broth, and repeated or fed batch fermentations; (2) a high productivity of 3 g/L/h was achieved from the batch culture at the high biomass concentration of 17.4 g/L; (3) repeated batch culture with a sole carbon source has been shown to be a favorable fermentation method in terms of enhancing the efficiency of lactic acid production. Lactic acid productivity and yields from the first seven batches reached the averages of 2.4 g/L/hr and 71%, respectively; (4) the fed batch culture had the highest lactic acid yield and lactic acid concentration of 86% and 138 g/L, respectively, while its overall productivity was 1.4 g/L/h.

Example 4

Prediction of Pellet Formation Using Logistic Regression Model

A multiple logistic regression model was used to predict the probability of occurrence of pellet formation. The multiple logistic response functions were expressed as equations (1) and (2).

$$E\{Y_i\} = \frac{\exp(\beta X_i)}{1 + \exp(\beta X_i)} \quad (1)$$

$$\beta X_i = \beta_0 + \beta_1 X_1 + \beta_2 X_2 + \beta_3 X_3 + \ldots + \beta_{21} X_{28} \quad (2)$$

where $Y_i$ are independent Bernoulli random variables with expected values $E\{Y_i\}$; the $X_i$ are different predictor variables and interaction effects, and the coefficients, $(\beta_i)$, are the parameters to be estimated by fitting the logistic model to the experimental data. The predictor variables could be quantitative or qualitative (Neter et al., 1996). Factors such as carbon source, inoculum size, temperature, shaking speed, addition of biodegradable polymers, neutralizer, spore storage time and their interactions on pellet formation were the predictor variables. Logistic regression was accomplished using the Statistical Analysis System program 9.0 (SAS institute Inc., NC). Backward stepwise selection was employed to fit the logistic regression equation. The significance of the coefficients was evaluated with individual coefficients being eliminated from the whole model if the p-value was greater than 0.2. The statistic analysis elucidated that temperature was a non-significant variable and that most of the interaction terms (except the interaction between PDB concentration and inoculum spore concentration) were non-significant variables. Thus, the significant variables of pH control, PDB concentration, spore concentration, shaking speed, polymer addition, culture time and the interaction of PDB and spore were included in the model.

TABLE 4

Analysis of maximum likelihood estimates of reduced model[a]

| Parameter | Estimate | Standard error | Wald Chi-Square | P > Chi Square |
|---|---|---|---|---|
| Intercept ($\beta_0$) | 179.5 | 79.8749 | 5.0516 | 0.0246 |
| pH ($\beta_1$) | 6.4594 | 2.9779 | 4.7050 | 0.0301 |
| PDB ($\beta_2$) | −28.9887 | 10.9882 | 6.9600 | 0.0083 |
| Spore ($\beta_3$) | −16.9952 | 7.5509 | 5.0658 | 0.0244 |
| PDB * spore ($\beta_{15}$) | 3.4649 | 1.3157 | 6.9357 | 0.0084 |
| Shaking speed ($\beta_5$) | −0.5332 | 0.2631 | 4.1060 | 0.0427 |
| Polymer ($\beta_6$) | 2.8114 | 1.0136 | 7.6935 | 0.0055 |
| Time ($\beta_7$) | 0.1478 | 0.0531 | 7.7631 | 0.0053 |

[a]Effects met the 0.20 significance level for entry into the model.

References

Arcidiacono, S., and Kaplan, D. L. 1992. Molecular weight distribution of chitosan isolated from Mucor rouxii under different culture and processing conditions. Biotechnology and Bioengineering 39: 281-286.

Bloomquist, J. 2001. RIS Metropolis Monte Carlo studies of poly (L-lactic), poly (L, D-lactic) and polyglycolic acids. Polymer 42:3515-3521.

Byrne, G. S., and O. P. Ward. 1989b. Growth of *Rhizopus arrhizus* in fermentation media. J. Ind. Microbiol. 4:155-161.

Byrne, G. S., and O. P. Ward. 1989a. Effect of Nutrition on pellet formation by *Rhizopus arrhizus*. Biotechnology and Bioengineering. 33: 912-914.

Calam, C. T. 1976. Starting investigational and production cultures. Process Biochemistry. 4: 7-12.

Cao, N., J. Du, C. S. Gong, and G. T. Tsao. 1996. Simultaneous production and recovery of fumaric acid from immobilized *Rhizopus oryzae* with a rotary biofilm contator and an adsorption column. Applied and Environmental Microbiology. 62: 2926-2931.

Carlile, M. J., Watkinson, S. C., Gooday, G. W., 2001. The Fungi. 2nd ed. Academic Press, London, U.K Casas Lopez, J. L., J. A. Sanchez Perez, J. M. Fernandez sevilla, F. G. Acien Fernandez, E. Molina Grima, Y. Chisti. 2004. Fermentation optimization for the production of lovastatin by *Aspergillus terreus*: Use of response surface methodology. Journal of Chemical Technology and Biotechnology. 79(10): 1119-1126.

Chahal, D. S. 1985. Solid-state fermentation with *Trichoderma reesei* for cellulase production. Applied and Environmental Microbiology. 49(1): 205-210.

Charles, M. 1978.Technical aspects of the rheological properties of microbial cultures. Adv. Biochem. Eng. 8: 417-437.

Doran, P., 1995. Bioprocess engineering principles. Academic Press, London.

Foster, J. W. and S. A. Waksman. 1939. The specific effect of zinc and other heavy metals on growth and fumaric acid production by *Rhizopus*. Journal of Bacteriology 37:599-617.

Galbraith, J. C., and J. E. Smith. 1969. Sporulation of *Aspergillus niger* in submerged liquid culture. Journal of General Microbiology. 59(1): 31-45.

Hang, Y. D. 1989. Direct fermentation of corn to L (+)-lactic acid by *Rhizopus oryzae*. Biotechnology Letters. 11(4): 299-300.

Jackson, S. L., and I. B. Heath. 1993. Roles of calcium ions in hyphal tip growth. Microbiol. Rev. 57(2): 367-382.

Kenealy, W., Zaady, E. and Du preez, J. C. et al. 1986. Biochemical aspects of fumaric acid accumulation by *Rhizopus arrhizus*. Appl. Environ. Microbiol. 52. 128-133.

Khor, E. 2001. Chitin: fulfilling a biomaterials promise. Elsevier, London.

Konig, B., K. Schugerl, and C. Seewald. 1982. Strategies for penicillin fermentation in tower-loop reactors. Biotechnology and Bioengineering. 24(2): 259-280.

Litchfield, J. H. 1996. Microbiological production of lactic acid. Advances in Applied Microbiology 42:45-95.

Liu, Y., Z. Wen, W. Liao, C. Liu, and S. Chen. 2005. Optimization of the process for the production of L(+)-lactic acid from cull potato by *Rhizopus oryzae*. Engineering in Life Sciences 5:343-349.

Liu, Y., W. Liao, C. Liu, and S. Chen. 2006. Optimization of L-(+)-lactic acid production using pelletized filamentous *Rhizopus oryzae* NRRL 395. Applied Biochemistry and Biotechnology 129-132:844-853.

Lopez-Malo, A., and E. Palou. 2000. Modeling the growth/no-growth interface of *Zygosaccharomyces baili* in Mango Puree. Food Microbiology and Safety. 65: 516-520.

Magnuson, Jon K. and Linda L. Lasure. 2004. Organic Acid Production by Filamentous Fungi, p. 307-340. In Lene Lange (ed.), Advances in Fungal Biotechnology for Industry, Agriculture, and Medicine. Kluwer Academic/Plenum Publishers.

Martin, S. M., and W. R. Waters. 1952. Production of citric acid by submerged fermentation. Journal of Industrial and Engineering Chemistry. 44: 2229-2233.

Metz, B., and N. W. F. Kossen. 1977. The growth of molds in the form of pellets—a literature review. Biotechnology and Bioengineering. 19(6): 781-799.

Muzzarelli, R. A. A., Leuniaux, R., Gooday, G., 1985. Chitin in Nature and Technology. Plenum Press, New York.

Neter, J., Kutner, M. H., Nachtsheim, C. J., and W. Wasserman. 1996. Applied Linear Statistical Model. Chapter 14. 4th edition, McGraw Hill Inc. NY.

Nielsen, J., and M. Carlsen. 1996. Fungal pellets, p 273-293. In R. G. Willaert, G. V. Baron, L. De Backer (ed), Immobilised living cell systems. John Wiley & Sons Ltd.

Olsvik, E. S., Kristiansen, B., 1994. Rheology of filamentous fermentations. Biotechnology Advance: 12:1-39.

Papagianni, M. 2004. Fungal morphology and metabolite production in submerged mycelial processes. Biotechnology Advances. 22: 189-259.

Pirt, S. J., and D. S. Callow. 1959. Continuous-flow culture of the filamentous mold *Penicillium chrysogenum* and the control of its morphology. Nature. 184: 307-310.

Rhodes, R. A., Moyer, A. J. and Smith, M. L. et al. 1959. Production of fumaric acid by *Rhizopus arrhizus*. Appl. Microbiol. 7. 74-80.

Rhodes, R. A., Lagoda, A. A., Misenheimer, T. J. and Smith, M. L., et al. 1962. Production of fumaric acid in 20-liter fermentors. Appl. Microbiol. 10. 9-15.

Romano, A. H., Bright, M. M., Scott, W. E. 1967. Mechanism of fumaric acid accumulation in *Rhizopus nigricans*. J. Bacteriol. 93. 600-604.

Schuurmans, D. M., B. H. Olson, and C. L. San Clemente. 1956. Production and isolation of thermoviridin, an antibiotic produced by *Thermoactinomyces viridins*. sp. Applied Microbiology. 4(2): 61-66.

Skierve, E., and O. Brennhovd. 1992. A multiple logistic model for predicting the occurrence of *Campylobacter jejuni* and *Campylobacter coli* in water. Journal of Applied Bacteriology. 73: 94-98.

Steel, R., S. M. Martin, and C. P. Lentz. 1954. A standard inoculum for citric acid production in submerged culture. Canadian Journal of Microbiology. 1(3): 150-157.

Tsao, G. T., N. J. Cao, J. Du, and C. S. Gong. 1999. Production of Multifunctional Organic Acid from Renewable Resources. Advances in Biochemical Engineering 65:243-280.

Tsuji, F. 2002. Autocatalytic hydrolysis of amorphous-made polylactides: effects of L-lactide content, tacticity, and enantiomeric polymer blending. Polymer 43:1789-1796.

Vaidyanathan, S., Arnold, S., Matheson, A. L., Mohan, P., McNeil, B. and Harvey L. M. 2000. Assessment of near-infrared spectral information for rapid monitoring of bioprocess quality Biotechnol. Bioeng. 74: 376-388.

Yin P. M., Yahiro, K., Ishigaki, T., Park, Y., and Okabe, M. (1998). L(+)-Lactic acid production by repeated batch culture of *Rhizopus oryzae* in air-lift bioreactor. J. Ferment. Bioeng. 85: 96-100

Yin, P. M., Nishina, N., Kosakai, Y., Yahiro, K., Park, Y., and Okabe, M. 1997. Enhanced production of L(+)-lactic acid from corn starch in a culture of *Rhizopus oryzae* using an air-lift bioreactor. J. Ferment. Bioeng. 84: 249-253.

Yusof, N. L. B. M., L. Y. Lim, and E. Khor. 2001. Preparation and characterization of chitin beads as a wound dressing precursor. Journal of Biomedical Materials Research 54:59-68.

Zhou, Y., J. Du., and G. T. Tsao. 2000. Mycelial pellet formation by *Rhizopus oryzae* ATCC 20344. Applied Biochemistry and Biotechnology. 84-86: 779-789.

Znidarsic, P., R. Komel, and A. Pavko. 1998. Studies of a pelleted growth form of *Rhizopus nigricans* as a biocatalyst for progesterone 11 α-hydroxylation. Journal of Biotechnology. 60: 207-216.

Znidarsic, P., R. Komel, and A. Pavko. 2000. Influence of some environmental factors on *Rhizopus nigricans* submerged growth in the form of pellets. World Journal of Microbiology & Biotechnology. 16: 589-593.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of growing a filamentous fungus as pellets in liquid medium, comprising the steps of
providing a liquid medium, wherein said liquid medium comprises substrate particles selected from the group consisting of agricultural waste products, minerals, grains and seeds or parts thereof;
inoculating a quantity of spores of said filamentous fungus into said liquid medium;
incubating said liquid medium and said spores under conditions that allow
i) attachment of said spores to said substrate particles; and
ii) germination and growth of fungal mycelia on said substrate particles,
wherein growth of said fungal mycelia on said substrate particles results in the formation of fungal pellets.

2. The method of claim 1, wherein said substrate particles are biodegradable.

3. The method of claim 1, wherein said grains or seeds are selected from the group consisting of rice, wheat, millet, corn, barley, oats, buckwheat, rye, and flax seed.

4. The method of claim 1, wherein said substrate particles are rice hulls.

5. The method of claim 1, wherein said substrate particles are $CaCO_3$.

6. The method of claim 1, wherein a concentration of said substrate particles is in the range of 1-20 grams per liter.

7. The method of claim 1, wherein said liquid medium is a carbon nutrient broth.

8. The method of claim 1, wherein said liquid medium comprises a calcium salt.

9. The method of claim 1, wherein said quantity of spores in said liquid medium is in a range of from $1\times10^7$ to $1\times10^{10}$ spores per liter.

10. The method of claim 1, further comprising the step of storing said spores for a period of time ranging from 2 days to 1.5 years prior to said step of inoculating.

11. The method of claim 10, wherein said period of time is at least one week.

12. The method of claim 1, wherein a pH of said liquid medium is in the range of from 2.5 to 7.

13. The method of claim 1, wherein during said step of incubating said liquid medium includes a step of agitating said liquid medium.

14. The method of claim 1, wherein said filamentous fungus is selected from the group consisting of *Rhizopus* species, *Trichoderma* species, *Aspergillus* species, and *Phanerochaete* species.

15. The method of claim 1, wherein said fungal pellets are of a uniform size.

16. The method of claim 1, wherein said fungal pellets are of a uniform shape.

17. The method of claim 1, wherein said fungal pellets have a porosity of from 5% to 30%.

18. The method of claim 1, wherein said fungal pellets comprise predominantly mature cells.

19. The method of claim 1, wherein said fungal pellets comprise predominantly bud cells.

* * * * *